(12) United States Patent
Koo et al.

(10) Patent No.: US 7,075,642 B2
(45) Date of Patent: Jul. 11, 2006

(54) METHOD, STRUCTURE, AND APPARATUS FOR RAMAN SPECTROSCOPY

(75) Inventors: Tae-Woong T. Koo, San Francisco, CA (US); Mineo Yamakawa, Campbell, CA (US)

(73) Assignee: Intel Corporation, Santa Clara, CA (US)

(*) Notice: Subject to any disclaimer, the term of this patent is extended or adjusted under 35 U.S.C. 154(b) by 211 days.

(21) Appl. No.: 10/373,480

(22) Filed: Feb. 24, 2003

(65) Prior Publication Data

US 2004/0165187 A1    Aug. 26, 2004

(51) Int. Cl.
G01J 3/44    (2006.01)
(52) U.S. Cl. .................................................. 356/301
(58) Field of Classification Search ................ 356/301, 356/300
See application file for complete search history.

(56) References Cited

U.S. PATENT DOCUMENTS

| | | | |
|---|---|---|---|
| 4,674,878 A | 6/1987 | Vo-Dinh | |
| 5,255,067 A | 10/1993 | Carrabba et al. | |
| 5,306,403 A | 4/1994 | Vo-Dinh | |
| 6,002,471 A | 12/1999 | Quake | |
| 6,081,328 A | 6/2000 | Eng | |
| 6,174,677 B1 | 1/2001 | Vo-Dinh | |
| 6,248,539 B1* | 6/2001 | Ghadiri et al. | 435/7.1 |
| 6,406,777 B1 | 6/2002 | Boss et al. | |
| 6,623,977 B1* | 9/2003 | Farquharson et al. | 356/301 |
| 2003/0231304 A1* | 12/2003 | Chan et al. | 356/301 |

OTHER PUBLICATIONS

Smith et al. (1992) *J. Appl. Phys.* 71:R1-R22.
Hummel et al. (1993) *Appl. Phys. Lett.* 63:2771-2773.
Masuda et al. (1995) *Science* 268:1466-1468.
Nassiopoulos et al. (1995) *Phys. Stat. Sol.* 190:91-95.
Zaidi et al. (1995) *Mat. Res. Soc. Symp. Proc.* 358:957-968.
Kim et al. (1996) *J. Vac. Sci. Technol.* 14:1906-1909.
Buttard et al. (1997) *Thin Solid Films* 297:233-236.
Cullis et al. (1997) *J. Appl. Phys.* 82:909-965.
Jessensky et al. (1997) *Thin Solid Films* 297:224-228.
Moreno et al. (1997) *Appl. Phys. Lett.* 71:2166-2168.

(Continued)

Primary Examiner—Gregory J. Toatley, Jr.
Assistant Examiner—Kara Geisel
(74) Attorney, Agent, or Firm—Julia A. Hodge

(57) ABSTRACT

Disclosed herein are a Raman spectroscopy structure comprising a porous material substrate, and a method of performing Raman spectroscopy of a sample disposed adjacent to the structure comprising the porous material substrate. Generally, the substrate includes one or more layers of a porous material such as porous silicon, porous polysilicon, porous ceramics, porous silica, porous alumina, porous silicon-germanium, porous germanium, porous gallium arsenide, porous gallium phosphide, porous zinc oxide, and porous silicon carbide. It has been discovered that such a substrate material, when excited with near-infrared light, does not exhibit undesired background fluorescence characteristic of other known Raman spectroscopy substrates.

31 Claims, 3 Drawing Sheets

OTHER PUBLICATIONS

Trau et al. (1997) *Nature* 390:674-676.
Chan et al. (1999) *Appl. Phys. Lett.* 75:274-276.
Kuzik et al. (1999) *Appl. Phys. Lett.* 75:1830-1832.
Li et al. (1999) *Adv. Mater.* 11:483-487.
Mattei et al. (1999) *Surface Science* 427-428:235-238.
Schuurmans et al. (1999) *Science* 284:141-143.
Terada et al. (1999) *4th Int'l Conf. on Ecomaterials* P-30:559-562.
Buzynin et al. (2000) *Technical Physics* 45:650-652.
Chan et al. (2000) *Proc. of SPIE* 3912:23-34.
Kamenev et al. (2000) *Semiconductors* 34:728-731.
Kim et al. (2000) *Jpn. J. Appl. Phys.* 39:5875-5878.
Korsunskaya et al. (2000) *ASDAM* 2000:339-342.
Lubberhuizen et al. (2000) *Journal of Porous Materials* 7:147-152.
Nielsch et al. (2000) *Adv. Mater.* 12:582-586.
Sangsig et al. (2000) *Jpn. J. Appl. Phys.* 39:5875-5878.
Spanier et al. (2000) *Appl. Phys. Lett.* 76:3879-3881.
Spanier et al. (2000) *Physical Review* 61:10437-10450.
Islam et al. (2001) *Appl. Phys. Lett.* 78:715-717.
Ohji (2001) *AIST Today* 1:28-31. (English-language abstract).
Dougherty et al.(2002) *Mat. Res. Soc. Symp. Proc.* 687:B. 7.3.6.
Mason et al. (2002) *Thin Solid Films* 406:151-158.
Matousek et al. (2002) *J. Raman Spectrosc.* 33:238-242.
Van Vugt et al. (2002) *Chem. Commun.* 2002:2054-2055.

* cited by examiner

METHOD, STRUCTURE, AND APPARATUS FOR RAMAN SPECTROSCOPY

BACKGROUND OF THE DISCLOSURE

1. Field of the Invention

The invention generally relates to the field of Raman spectroscopy and, more specifically, to porous substrates suitable for use in Raman spectroscopy apparatus.

2. Brief Description of Related Technology

Spectroscopy is an analytical technique useful to measure the radiant energy absorbed or emitted by a substance in response to excitation by an external energy source, and to translate that measurement into meaningful spectra. Interpretation of the spectra is useful to determine fundamental information about the substance, such as, for example, its composition, atomic and molecular energy levels, molecular structures and their geometries, chemical bonding, and interactions between molecules. This interpretation generally is carried out by comparing the spectra obtained from an unknown substance to the spectrum of a known substance. Such comparisons provide a basis from which a skilled artisan can determine the chemical composition and chemical structure of the unknown substance.

The types of absorption and emission spectroscopy are usually identified by reference to the associated wavelength, such as, for example, gamma-ray, infrared (IR), microwave, radiofrequency, ultraviolet (UV), visible, and x-ray. Highly-specialized techniques have been developed since the inception of spectroscopic analysis in the 19th Century, including, for example, dynamic reflectance spectroscopy, electron paramagnetic resonance, gamma-ray spectroscopy, IR spectroscopy, laser, microwave, nuclear magnetic resonance, nuclear quadrupole resonance, and Raman spectroscopy. See generally, Hawley's Condensed Chemical Dictionary, 12th ed., Van Nostrand Reinhold, New York, p. 1039 (1997).

One particular spectroscopic technique, known as Raman spectroscopy, is based on the detection of optical energy (e.g., light) that has been scattered by a substance (e.g., a molecule) when excited by an external energy source (e.g., a laser). This scattering is commonly known as the "Raman effect." When exciting optical energy of a single wavelength (e.g. monochromatic light) interacts with a molecule, for example, the optical energy scattered by the molecule contains small amounts of optical energy having wavelengths different from that of the incident, exciting optical energy. The wavelengths of the scattered optical energy are characteristic of the molecule's structure, and the intensity of the scattered optical energy is related to the concentration of the molecule. The wavelengths are separated by a spectrometer and detected by a detector to provide a Raman spectrum. The output of the detector can be interpreted with the aid of a data processor (e.g., a computer). Each different molecule has its own unique Raman spectrum, which can be used for both qualitative (e.g., identification) and quantification (e.g., determination of concentration) purposes.

Historically, Raman spectroscopy has been a useful spectrochemical technique for chemists in characterizing the chemical make-up of various substances and in identifying unknown molecules. Raman spectroscopy is a technique that is complementary to IR spectroscopy. Due to differences in the spectroscopic selection rules, each is sensitive to different components of a given sample. For example, IR spectroscopy generally is more sensitive to polar bonds (e.g., oxygen-hydrogen bonds), while Raman spectroscopy is more sensitive to vibrations of carbon backbone structures and symmetrical bonds (e.g., $C=C$ groups). Using both spectroscopic techniques to characterize a particular sample may provide information on the sample's chemical composition that might not be obtainable using either of the techniques alone.

More recently, Raman spectroscopy has been used in the biological and other life-sciences areas including, but not limited to, analyses of the stratum corneum in human skin in relation to the administration of therapeutic agents, cancer diagnosis, corneal dehydration in relation to impaired visual acuity, characterization of gallstones and kidney stones, diagnosis of Alzheimer's disease, diagnosis of metabolic disorders by taking Raman spectra of hair and nails, hard tissue implant biocompatibility and in vivo recovery characteristics, imaging of cells (e.g., carotenoids in lymphocytes), and quantitative histochemical analysis of human arteries. Raman spectroscopy also has been implicated as a useful technique in DNA sequencing and in deciphering the human genome. The need for powerful and costly laser sources for excitation and other prohibitively costly equipment in these and other biological and chemical analyses limit the practicality of conventional Raman spectroscopy apparatus.

Conventional Raman spectroscopy of an unpurified sample may detect that the sample gives a broad optical emission signal, much of which is attributable to undesired background fluorescence. Background fluorescence also can be attributed to known fluorophores, trace amounts of adventitious fluorescent impurities in the sample, and from the substrate on which the sample is analyzed. In Raman spectroscopy, such background fluorescence is undesired because it drowns out the relatively weak Raman signal(s) attributable to the target molecule.

One approach to dealing generally with the undesired background fluorescence is to perform background subtractions to discount this fluorescence from the obtained spectrum. However, because Raman signals oftentimes are so weak relative to the background fluorescence, it is difficult to make meaningful and accurate determinations even when discounting the background fluorescence. This difficulty is only exacerbated where the target molecule is present in very low concentrations. Another approach is to avoid the fluorescence by utilizing an excitation energy source in the near-infrared (NIR) region in the absence of electronic absorption and emission transitions. This approach, however, does not permit the resonance effect of Raman spectroscopy to be utilized for many compounds and also suffers from low sensitivity owing to the inverse fourth-power law dependence of non-resonant Raman scattering. Yet another approach is to utilize an excitation energy source well below the fluorescence emission in the UV region. Though this approach desirably permits much higher cross-sections for Raman scattering than in the NIR region, it often leads to resonance enhancement of several constituents of the substance simultaneously, which is undesirable when trying to detect and/or characterize molecules present at low concentration or where molecular selectivity is desired. Other approaches include utilizing surface-enhanced Raman spectroscopy (SERS), shifted excitation Raman difference spectroscopy (SERDS), polarization modulation, shifted spectra, Fourier transform filtering, and temporal gating. See generally, Matousek et al. (2002) *J. Raman Spectrosc.* 33:238–242. High expense, high complexity, and/or low reproducibility, however, are undesirable characteristics of each of these approaches.

An approach to combating undesired background fluorescence attributable to the substrate is to utilize a substrate that does not generate interfering signals and/or a substrate having a microcrystalline surface. Such substrates, however, must be of high purity and, thus, are more expensive. Even where one is able to afford substrates having the desired microcrystalline surface, such substrates can only be manufactured to a certain size and, therefore, Raman spectroscopy applications are limited by such size limitations. To diminish the effects of background fluorescence caused by the substrate, the target molecule(s) may be floated in air or water to spatially separate the target molecule(s) from the substrate material—this permits a spatial separation of the Raman signal(s) of the molecule(s) from the interfering signal(s) generated from the substrate. This approach, however, undesirably includes the additional steps of utilizing a liquid or gas to spatially separate the target molecule(s) from the substrate and accompanying associated equipment.

BRIEF DESCRIPTION OF THE DRAWING FIGURES

For a more complete understanding of the disclosure, reference should be made to the following detailed description and accompanying drawing figures wherein.

Figure 1:
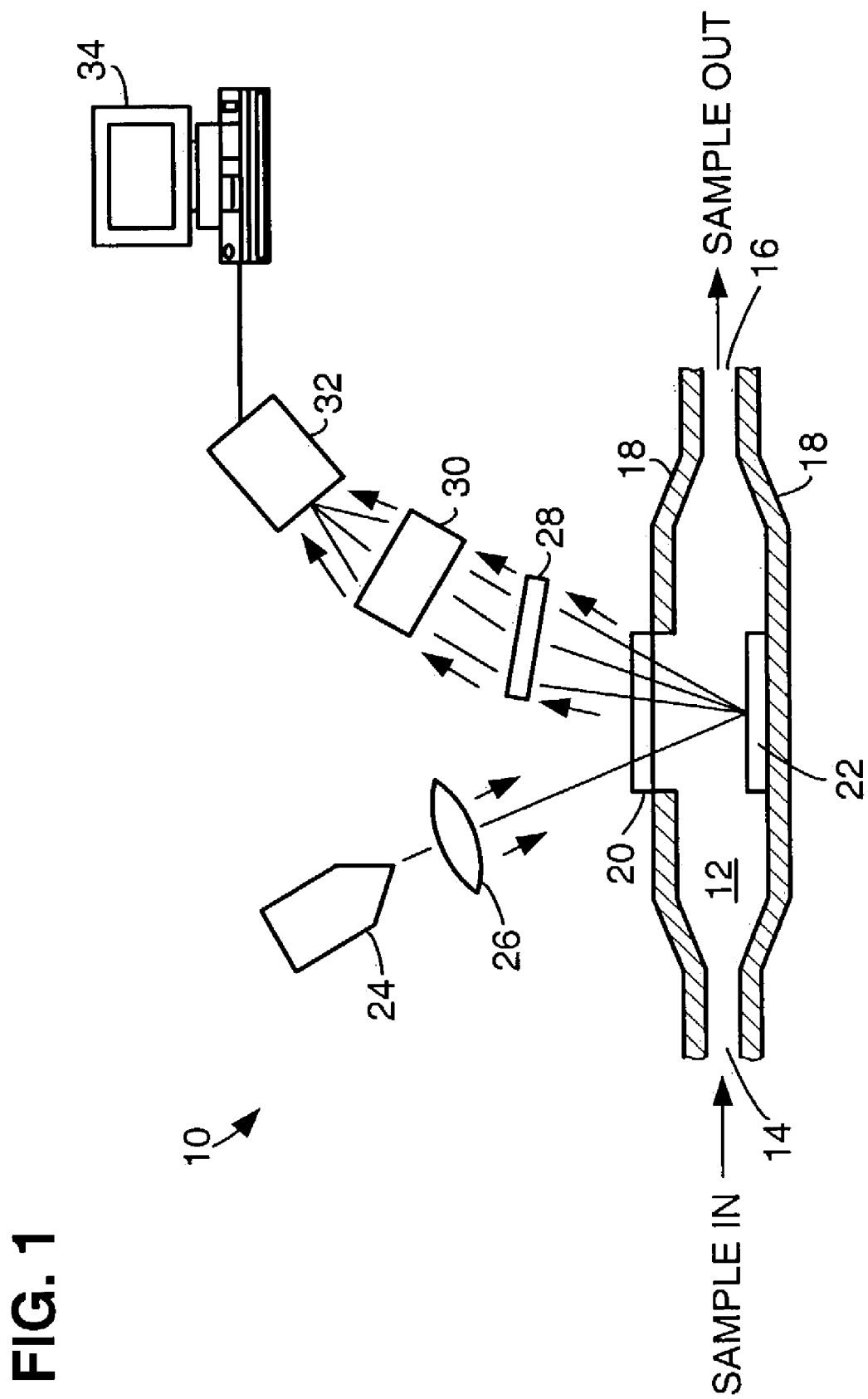
FIG. 1 illustrates Raman spectroscopy apparatus comprising a porous silicon substrate.

While the disclosed structure, substrate, apparatus, and method are susceptible of embodiments in various forms, there are illustrated in the drawing figures (and will hereafter be described) specific embodiments of the disclosure, with the understanding that the disclosure is intended to be illustrative, and is not intended to limit the invention to the specific embodiments described and illustrated herein.

DETAILED DESCRIPTION OF THE PREFERRED EMBODIMENTS

Disclosed herein are a structure and substrate for use in Raman spectroscopy, associated Raman spectroscopy apparatus, and methods of performing Raman spectroscopy. Generally, the structure includes a substrate that is a porous material containing microporous structures or layers. Suitable porous materials include porous silicon (e.g., single crystal porous silicon), porous polysilicon, porous ceramics (e.g., those made from fibrous porous silicon nitride), porous silica, porous alumina, porous silicon-germanium, porous germanium, porous gallium arsenide, porous gallium phosphide, porous zinc oxide, and porous silicon carbide. Methods of making such porous materials are generally known by those having ordinary skill in the art. See, for example, Dougherty et al. (2002) *Mat. Res. Soc. Symp. Proc.* 687: B.7.3.1–B.7.3.6 (porous polysilicon), Ohji (2001) *AIST Today* 1:28–31 (porous ceramics), Trau et al. (1997) *Nature* 390:674–676 (porous silica), Masuda et al. (1995) *Science* 268:1466–1468 (porous alumina), Li et al. (1999) *Adv. Mater.* 11:483–487 (porous alumina), Nielsch et al. (2000) *Adv. Mater.* 12:582–586 (porous alumina), Buttard et al. (1997) *Thin Solid Films* 297:233–236 (porous silicon-germanium), van Vugt et al. (2002) *Chem Commun.* 2002: 2054–2055 (porous germanium), Kamenev et al. (2000) *Semiconductors* 34:728–731 (porous gallium arsenide), Buzynin et al. (2000) *Tech. Physics* 45:650–652 (porous gallium arsenide), Shuurmans et al. (1999) *Science* 284: 141–143 (porous gallium phosphide), Lubberhuizen et al. (2000) *J. Porous Mat.* 7:147–152 (porous gallium phosphide), Terada et al. (1999) *4th Int'l. Conf. on Ecomaterials* P-30:559–562 (porous zinc oxide), Jessensky et al. (1997) *Thin Solid Films* 297:224–228 (porous silicon carbide), Spanier et al. (2000) *Appl. Phys. Lett.* 76:3879–3881 (porous silicon carbide), Spanier et al. (2000) *Physical Review B* 61:10437–10450 (porous silicon carbide), and Sangsig et al. (2000) *Jpn. J. Appl. Phys.* 39:5875–5878 (porous silicon carbide). The substrate can include a plurality of layers of the porous material.

The structure also can include other materials adjacent to the substrate, such as metals, crystals, polymers, and optical glass. Suitable metals include, but are not limited to, aluminum, copper, gold, iridium, nickel, palladium, platinum, rhodium, silver, steel, titanium, tungsten, zinc, and alloys thereof. Suitable crystals include, but are not limited to, magnesium fluoride, calcium fluoride, quartz, diamond, sapphire, germanium, and ZnSe. Suitable polymers include, but are not limited to, polydimethylsiloxane and plastics. Suitable optical glass materials include those commercially available from, for example, Schott Glass (Germany) under the names BK7, SFL11, BaK4, F2, SK5, SF2, SF1, and LASF35. Additional, suitable optical glass materials include, but are not limited to, crown, flint, soda lime glass, flat glass, and borosilicate glass. Any one or more of the foregoing materials may be a part of the structure depending upon the handling and/or structural integrity characteristics desired of the structure.

A preferred porous material is porous silicon. Porous silicon is a material that can be made simply and inexpensively, and can be defined by an array containing nanocrystalline silicon objects of different sizes. As observed by high resolution scanning and transmission electron microscope, porous silicon typically has pore diameters varying from a few nanometers to several micrometers, depending upon the conditions under which the porous silicon was formed. The term "porous" as used herein may be defined consistent with the IUPAC guidelines, wherein "microporous" refers to pores having a size regime that is less than or equal to two nanometers (nm), "mesoporous" refers to pores having a size regime that is between about 2 and 50 nm, and "macroporous" refers to pores having a size regime that is greater than about 50 nm. See e.g., Cullis et al. (1997) *J. Appl. Phys. Rev.* 82:909–965.

The term "conversion efficiency" as used herein refers to a measurement indicating the amount of fluorescence signal generated for an incoming wavelength of excitation light. A conversion efficiency of 0.0001 percent per nanometer (% per nm) indicates that for one million photons of excitation light, one photon is emitted as an interfering fluorescence signal over one nanometer wavelength range. Thus, for excitation light in the wavelength range between about 850 nm and about 1020 nm, a conversion efficiency of 0.0001% per nm indicates that there will be 170 interfering photons emitted over the spectral range per one million excitation photons. The conversion efficiency can be converted to a unitless value (referred to herein as "relative intensity") and plotted over a wavelength range, such as in FIGS. 3 through 5, for purposes of more easily visualizing fluorescence signal.

The nature of the substrate disclosed herein is characterized by its porosity, i.e., the relative volume fraction occupied by the pores (expressed as a percentage). Depending upon the wafer and the manufacturing conditions, the morphology of the porous material can be either "sponge-like" or "columnar." Where the morphology is "sponge-like," pores having dimensions that range from several microns in width to only a few nanometers are randomly distributed in the film. The pores are defined by crystalline walls anchored to the floor of the wafer. Micron-sized pores also may be columnar. Where the morphology is "columnar," there are long pores of typically 15 nm diameter defined by walls approximately running parallel to the <100> direction of the lattice, wherein the walls have a thickness of less than about 20 nm, and preferably about 5 nm to about 10 nm. The size and orientation of the pores can be controlled by the etching conditions, as described herein. However, virtually all porous layers will exhibit some non-homogeneity with depth, i.e., a finite porosity gradient exists. Porous layers may exhibit a negative porosity gradient depending on the etching conditions, i.e., the porosity will decrease with increasing depth within the layer, and is highest at its surface. Generally, the thickness of the porous material is about 10 nm to about 500 micrometers (elm), more preferably about 200 nm to about 100 μm, and even more preferably about 400 nm to about 50 μm.

Porous materials, such as porous silicon, may be made by many different techniques, the most common of which is one using electrochemistry because a relatively large and relatively homogeneous substrate can be readily formed by such technique. Such size, homogeneity, and simplicity and economical manufacture make porous silicon extremely desirous over substrate materials previously used by those skilled in the art when performing Raman spectroscopy. Heretofore, silicon was known to be an extremely poor material for use as a substrate in Raman spectroscopy Silicon has a band gap at the energy level corresponding to light of 1100 nm wavelength, which is within the near-infrared region (NIR) of about 700 nm to about 1300 nm. Furthermore, silicon absorbs light having a wavelength shorter than 1100 nm and generates interfering optical signals. See Example 2 and FIG. 5 herein. Light emitted by silicon is particularly strong when the excitation energy source emits light at a wavelength in the near-infrared region that is close in proximity to the band gap of silicon (e.g., between 700 nm and 1100 nm). With shorter wavelength excitation light (e.g., 514 nm wavelength light from an argon-ion laser), however, suitable Raman spectroscopy may be possible, but less desirable. Use of near-infrared light (as opposed to shorter wavelength excitation light) as an excitation energy source has been found to be attractive because its energy level is less than that of visible or UV light, and because such near-infrared light does not generate interfering fluorescence signals from the sample, nor is it as likely to damage the sample. In view of the poor performance of silicon with NIR light, however, those skilled in the art would not utilize silicon as a substrate for Raman spectroscopy.

It has now been discovered that the porous materials disclosed herein, such as, for example, porous silicon, unexpectedly serve as an excellent substrate and suppress (or do not exhibit) the type of background fluorescence commonly characteristic of other substrates, such as conventional metal substrates and the like. Such porous materials are especially effective as a substrate (or a Raman scattering structure) in Raman spectroscopy apparatus. Specifically, in one embodiment, the substrate comprises a porous silicon material capable of exhibiting Raman scattering of the sample and wherein the substrate preferably exhibits a conversion efficiency of less than about 0.0001% per nm in a wavelength range between about 850 nm and about 1020 nm. More preferably, the substrate exhibits a conversion efficiency of less than about 0.000075% per nm, and even more preferably the substrate exhibits a conversion efficiency of less than about 0.00005% per nm, and still even more preferably, the substrate exhibits a conversion efficiency of less than about 0.00001% per nm in a wavelength range between about 850 nm and about 1020 nm.

In the manufacture of porous silicon substrates, suitable silicon materials include n-type or p-type silicon wafers, preferably having a <100> grown single crystal structure. For example, a boron-doped wafer is a type of p-type silicon wafer. Typically, a highly boron-doped silicon wafer (p+, about 0.01 Ohm-cm) is chosen because the range of porosities that can be formed is wide (e.g., about 30% to about 95%). Preferably, the formed substrate has at least one porous silicon layer having a porosity of about 45% to about 85%, and more preferably about 60% to about 80%. Using an effective medium approximation, a broad ranging porosity of about 30% to about 95% will likely result in a refractive index of about 3 to about 1.

While porous silicon substrates can be prepared by a variety of techniques, such as, for example, stain etching and anodic etching, preferably, porous silicon substrates are prepared by anodic electrochemical etching. Anodic electrochemical etching permits one to carefully control properties of the formed substrate such as, for example, microstructure, pore diameter, porosity, refractive index, and thickness. Anodic electrochemical etching includes immersing an electrode (e.g., a platinum electrode) and a silicon wafer in an electrolytic bath containing, for example, water, ethanol, and hydrofluoric acid (HF), or solutions of hydrogen nitrate ($HNO_3$) in HF. While in solution, the wafer is subjected to a constant current in a range of about 1 $mA/cm^2$ to about 1000 $mA/cm^2$, preferably about 5 $mA/cm^2$ to about 500 $mA/cm^2$. The current is applied to the wafer for a time period ranging from several seconds to several hours, preferably for up to about one hour, to form a layer of porous silicon at or on the surface of the wafer. Etching and anodization can occur with or without illumination depending upon the type of substrate dopant. After anodization, the porous wafer is removed, rinsed, and dried leaving a porous silicon layer etched into the wafer. Drying may occur by way of atmospheric drying, nitrogen gas drying, supercritical drying, freeze drying, or by polymerization of pore liquids. To ensure that the morphology of the formed substrate remains intact, the substrate should be stored in vacuum, under an inert atmosphere, or under such other conditions so as not to affect the morphology. Reproducibility and the electronic, optical, and structural characteristics of the formed porous silicon are dependent upon various processing conditions, such as, for example, the electrolyte composition and temperature, current density, the applied current, and the resistivity of the wafer.

With respect to the electrolyte composition, ethanol is commonly added to the HF to minimize hydrogen bubble formation during anodization and, thus, improves layer uniformity. Ethanol also improves wettability and helps HF to better infiltrate into the pores. Electrolyte compositions containing dilute HF typically will provide layers having high porosity, while electrolyte compositions containing concentrated HF typically will provide layers having low porosity. The electrolyte preferably is at room temperature, such as, for example, about 15° C. to about 25° C. Etching at lower temperatures such as, for example, less than about 5° C., can be used to obtain higher levels of porosity.

Once porous silicon is formed, the inter-pore region is depleted of holes. Further dissolution should occur only at tips of the pores, where holes are still available. The dissolution of the silicon atoms is mainly restricted to the silicon/electrolyte interface and, therefore, the porous layer first formed should remain intact throughout subsequent etching. In this way, the etching of porous silicon proceeds in depth with an overall directionality that should follow the anodic current paths inside the silicon substrate. Multilayer structures typically are fabricated using a periodic current density square pulse during the electrochemical dissolution process. By pulsing between two different current densities, two different porosity porous silicon layers can be formed. For example, two different current densities, one of which is at about 5 milliamps per square centimeter ($mA/cm^2$) for 20 second period, and another of which is at 30 $mA/cm^2$ for a period of about 10 seconds, can be pulsed five times to produce 10 different layers of porous silicon.

The porosity is a linear function of the current density for a specific HF concentration and current density interval. Porosity values can be estimated using a porosity dependence on current density plot, and values for the thickness can be obtained through scanning electron microscope micrographs. For fixed values of porosities or refractive indices, the reflectivity of a multilayer substrate increases as the number of periods increases. Thus, for example, for a multilayer porous silicon substrate containing 6 periods, 88% reflectivity centered at 760 nm is attainable, and nearly 100% reflectivity is attainable for a multilayer porous silicon substrate containing 10 periods. Additional layers may be formed by employing additional current densities and appropriate pulsing.

After anodization, the porous silicon multilayer structures typically are stabilized by thermal oxidation in an oxygen atmosphere (ambient) at about 800° C. to about 1000° C. for about 5 minutes to about 20 minutes, preferably at about 850° C. to about 950° C. for about 8 minutes to about 15 minutes, more preferably at about 900° C. for about 10 minutes. Oxidation can induce a blue-shift in peak reflectivity due to a change in the refractive index of the layers. See generally, Moreno (1997) *Appl. Phys. Lett.* 71:2166–2168. For multilayer structures, it has been found that the peak reflectivity may not decrease upon thermal treatment.

Another technique by which porous silicon can be made is "spark erosion." Spark erosion is a dry technique in that it does not utilize aqueous solutions or hydrofluoric acid for sample preparation. In contrast to anodic, electrochemical etching, n- or p-type silicon wafers are subjected to high frequency/low current electric sparks. A counter electrode is constructed of the same material as the wafer to avoid any unintended contamination of the wafer, and the technique is carried out in air, or in a dried, high purity nitrogen atmosphere to reduce or prevent hydrogen involvement. Spark erosion treatment of single crystalline silicon wafers produces randomly oriented silicon nanocrystallites imbedded in a silica matrix. High-energy electric sparks cause localized redeposition of silicon leading eventually to nanometer size crystallites. See generally, Hummel et al. (1993) *Appl. Phys. Lett.* 63:2771–2773. For a general description of anodic, electrochemical etching techniques for making multilayer porous silicon substrates, reference should be made to Chan et al. (2000) *Proc. of SPIE* 3912:23–34, the disclosure of which is hereby incorporated herein by reference.

Porous silicon structures on a nanoscale can be made by an anisotropic etch with a solution of potassium hydroxide, for example, followed by high-temperature oxidation and oxide removal as described above. Such structures have silicon pillars having diameters less than about 10 nm and an aspect ratio of height to diameter as high as about 50:1. See generally, Nassiopoulus et al. (1995) *J. Phys. Stat. Sol.* 190:91–95; see also Zaidi et al. (1995) *Mat. Res. Soc. Symp. Proc.* 358:957–968.

Generally, a suitable Raman spectroscopy apparatus should include a light source and a structure that includes a substrate comprising a porous material (e.g., porous silicon) capable of exhibiting Raman scattered light of the sample. Suitable porous materials include porous silicon (e.g., single crystal porous silicon), porous polysilicon, porous ceramics (e.g., those made from fibrous porous silicon nitride), porous silica, porous alumina, porous silicon-germanium, porous germanium, porous gallium arsenide, porous gallium phosphide, porous zinc oxide, and porous silicon carbide. As stated above, a porous silicon substrate preferably exhibits a conversion efficiency of less than about 0.0001% per nm in a wavelength region between about 850 nm and about 1020 nm. As noted above, the structure also can include one or more other materials adjacent to the porous material substrate such as, for example, metals, crystals, polymers, and optical glass. The apparatus also should include one or more lenses for directing (e.g., focusing) the light onto a sample disposed adjacent to the structure/substrate and for collecting the Raman scattered light from the sample and substrate, and a spectroscopic analyzer capable of producing an electronic signal proportional to an intensity of the Raman scattered light in a fixed wavelength range or as a function of wavelength.

Referring now to the drawing figures, FIG. 1 schematically illustrates a suitable Raman spectroscopy apparatus 10. As illustrated in FIG. 1, a sample, such as a gas and/or liquid material, may enter a cell 12 through a cell entrance 14 and exit the cell 12 through a cell exit 16. The cell 12 is defined by a wall 18 and a cell window 20 contiguous with the wall 18. The cell 12 also includes a structure comprising a porous substrate 22 that typically is positioned on a wall surface opposite the cell window 20. The apparatus 10 includes an excitation light source, such as a laser 24, which directs light towards the cell window 20 through a lens 26 and onto the sample present in the cell 12 and the substrate 22 therein. The light emitted/scattered by the sample and the substrate 22 is directed through the cell window 20 and through a set of optical components (e.g., mirrors, lenses, and/or prisims) 28 and filter or spectrograph 30 to a single-element detector (e.g., a photodiode) or a multi-element detector (e.g., a CMOS detector or a charge-coupled-device (CCD) camera) 32, which communicates information concerning the emitted/scattered light to a device (e.g., a computer) 34 capable of plotting or otherwise translating the information as a Raman spectrum. Other suitable Raman spectroscopy apparatus utilizing a porous substrate as described herein may be utilized as well. Shown in FIG. 2 (and described in more detail below) is an scanning electron microscope (SEM) micrograph image of a porous silicon substrate for use with the Raman spectroscopy apparatus.

A method of performing Raman spectroscopy includes positioning a sample adjacent to a structure, the structure including the substrate comprising the porous material, directing light from the light source onto the substrate and the sample, and measuring an intensity of any Raman scattered light from the sample and the substrate. Additionally, the method can include producing an electronic signal proportional to the intensity of the Raman scattered light in a fixed wavelength range or as a function of a wavelength. Furthermore, the method can include translating the electronic signal into a Raman spectrum. As previously noted herein, the porous material is selected from the group consisting of porous silicon, porous polysilicon, porous ceramics, porous silica, porous alumina, porous silicon-germanium, porous germanium, porous gallium arsenide, porous gallium phosphide, porous zinc oxide, and porous silicon carbide.

EXAMPLES

Figure 3:
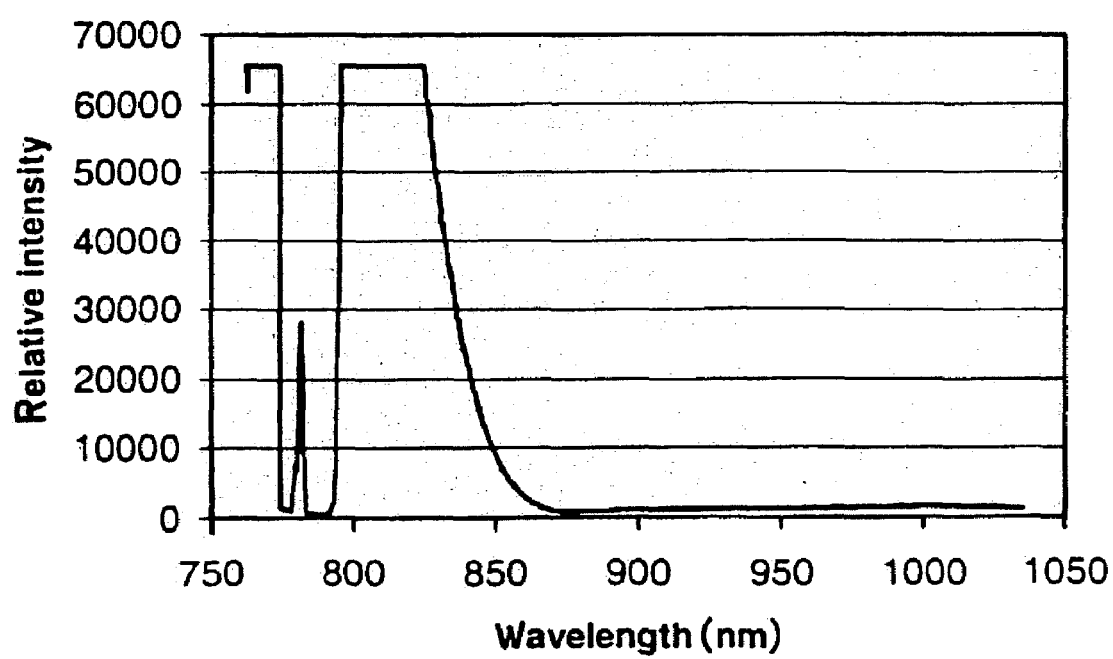
FIG. 3 is a graphical illustration of an optical emission spectrum for the porous silicon substrate shown in FIG. 2.
Figure 4:
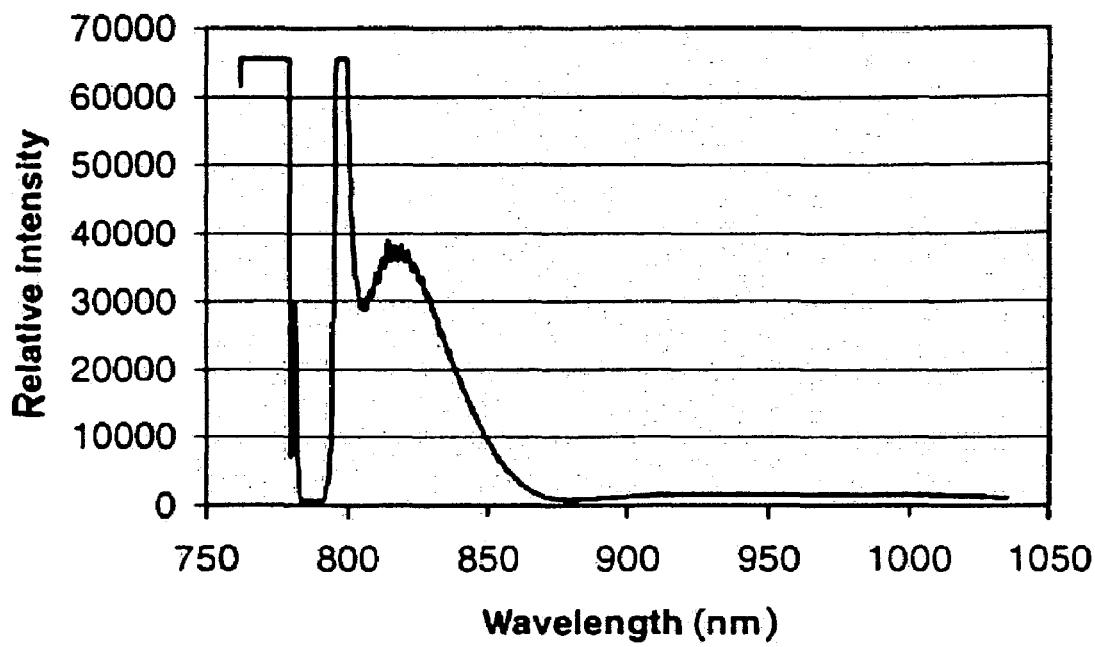
FIG. 4 is a graphical illustration of an optical emission spectrum for the porous silicon substrate shown in FIG. 2; and, FIG. 5 is a graphical illustration of an optical emission spectrum for a non-porous, bulk crystalline silicon.
Figure 5:
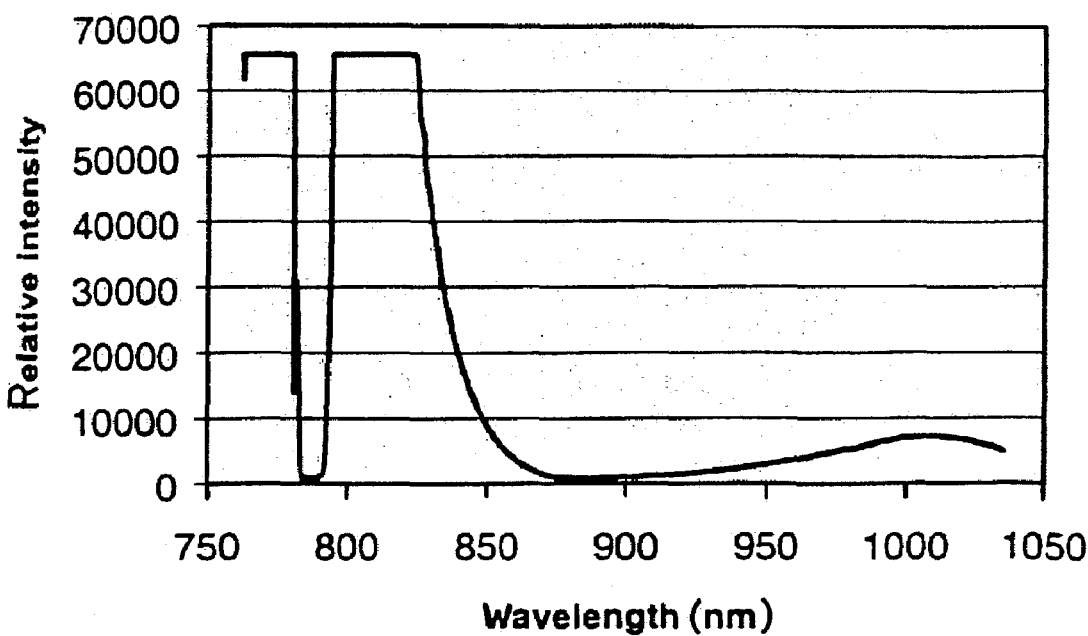

With respect to the following examples, apparatus similar to one schematically illustrated in FIG. 1 was used to generate the optical spectra shown in each of FIGS. 3 through 5. Specifically, the apparatus included a titanium:sapphire laser pumped by a diode-pumped solid-state laser, which produced an excitation light having a wavelength of about 785 nm. Spectra-Physics of Mountain View, Calif. manufactured the titanium:sapphire laser under the model name "Tsunami," and also manufactured the diode-pumped solid-state laser under the model name "MilleniaV." The excitation light was focused by a microscope objective, manufactured by Nikon, and impinged on the sample substrate. The Raman scattered light was collected by the same microscope objective, and was sent to a dichroic mirror and a notch filter, both of which were manufactured by Chroma of Brattleboro, Vt. The dichroic mirror spatially separated the back-scattered excitation light and the Raman-scattered light. The notch filter further reflected the excitation light, and only transmitted the Raman-scattered light. The filtered light was delivered to the spectrograph, which dispersed the light as a function of wavelength. The spectrograph was manufactured by Acton Research of Acton, Mass. The dispersed light was imaged by a liquid nitrogen-cooled, charge-coupled-device (CCD) camera, which was manufactured by RoperScientific of Princeton, N.J. The CCD camera was connected to a personal computer, and the collected spectrum was transported to the computer for visual display and computational analysis.

Example 1

Figure 2:
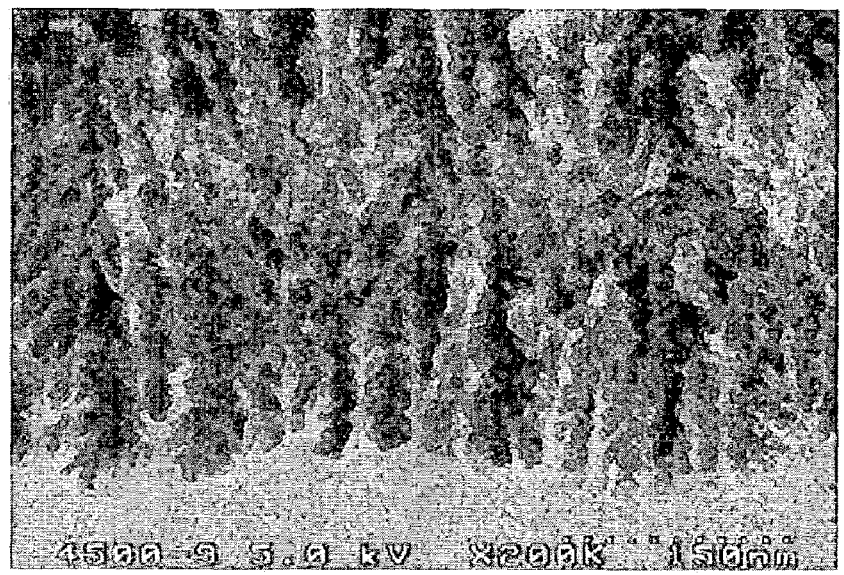
FIG. 2 is a scanning electron microscope (SEM) micrograph image of a porous silicon substrate suitable for use in Raman spectroscopy.

Shown in FIG. 2 is a scanning electron microscope (SEM) micrograph image of a porous silicon substrate for use with the Raman spectroscopy apparatus. The substrate was prepared by anodic, electrochemical etching, as described above. More specifically, the substrate was prepared by subjecting a highly boron-doped, p-type silicon wafer to etching in an aqueous electrolyte solution containing ethanol and HF present in a concentration of about 15 percent by volume based on the total volume of the solution (15% HF by volume). Anodization was carried out by a computer-controlled constant current applied across the cell (between a platinum cathode and the silicon anode). Multiple layers of porous silicon were produced from 5 periods of two different current density settings. One such setting was at 5 mA/cm$^2$ for 20 seconds, which provided a layer having a porosity of about 42% and a thickness of about 80 nm. The other setting was at 30 mA/cm$^2$ for 10 seconds, which provided a layer having a porosity of about 63% porosity, and a thickness of about 160 nm. The formed substrate was of a circular, disc shape with a diameter of about one inch. Though the formed substrate can generally be considered to be homogenous, there were slight variations (e.g., porosity, thickness, etc.) when comparing the center portion of the substrate to the edge portions of the substrate. Such layers may be attributable to the nature of layer-forming process. The slight variations are evident when comparing the optical emission spectra light (of about 1 micrometer in cross-sectional diameter) excited toward the center portion or the substrate (see FIG. 3) versus light excited toward the edge portions of the same substrate (see FIG. 4).

Shown in FIG. 3 is an optical emission spectrum of the multilayer porous silicon substrate shown in FIG. 2 with 785 nm excitation. The optical emission spectrum was obtained by the apparatus as described above, wherein the excitation light was directed to a center portion of the substrate. Referring to FIG. 3, those peaks present at wavelengths less than about 875 nm are attributable to optical components of the apparatus, such as, for example, the lens, the mirrors, the filters, etc. Importantly, the peaks at wavelengths above about 875 nm are not noticeable. Thus, this substrate does not exhibit any of the background fluorescence undesirably characteristic of other substrate materials.

Shown in FIG. 4 is an optical emission spectrum of the same multilayer porous silicon shown in FIG. 2 with 785 nm excitation. The optical emission spectrum was obtained by the apparatus as described above. In contrast to FIG. 3, however, the excitation light was directed to an edge portion of the substrate. In FIG. 4, all peaks present at wavelengths less than about 875 nm (with the exception of the peak present at about 820 nm) are attributable to optical components of the apparatus, such as, for example, the lens, the mirrors, the filters, etc. The peak present at about 820 nm is believed to be attributable to the substrate itself. However, the presence of this peak does not diminish the unexpectedly desirable benefits of porous silicon material in general. A peak present at about 820 nm will not interfere with the accuracy of peaks sought from a sample between the 850 nm and 1020 nm range. As in FIG. 3, the peaks at wavelengths above about 875 nm are not noticeable. Thus, even edge portions of this substrate do not exhibit any of the background fluorescence undesirably characteristic of other substrate materials.

Example 2 (Comparative Example)

To contrast the performance differences between porous silicon and that of non-porous silicon at NIR excitation wavelengths, a non-porous, bulk crystalline silicon substrate was placed in the identical apparatus. The silicon wafer was obtained from Polishing Corporation of America and was single-sided, polished, and boron-doped. The wafer had a <100> orientation by Czochralski growth and a resistivity of 0.008 to 0.012 Ohm-cm. The size of the wafer was 100 mm, and its thickness was 500 microns.

Shown in FIG. 5 is an optical emission spectrum of the non-porous, bulk crystalline silicon substrate with 785 nm excitation. The peaks present at wavelengths of about 900 nm to about 1040 nm are due to the fluorescence attributable solely to the substrate. This spectrum, when compared to those shown in FIGS. 3 and 4, clearly shows that porous silicon substrates in accordance with the disclosure desirably do not exhibit such fluorescence when excited with NIR light.

The foregoing description is given for clearness of understanding only, and no unnecessary limitations should be understood therefrom, as modifications within the scope of the disclosure may be apparent to those having ordinary skill in the art.

What is claimed is:

1. A Raman spectroscopy apparatus comprising:
    (a) a light source;
    (b) a structure comprising a substrate, the substrate comprising porous silicon wherein the porous silicon exhibits a conversion efficiency of less than about 0.0001% per nm in a wavelength range between about 850 nm and about 1020 nm;
(c) one or more lenses for directing light from the light source onto the substrate or for collecting Raman scattered light from the substrate and a sample; and,
(d) a spectroscopic analyzer capable of producing an electronic signal proportional to an intensity of the Raman scattered light in a fixed wavelength range or as a function of wavelength.

2. The apparatus of claim 1, wherein the porous silicon is a p-type silicon and the substrate comprises a plurality of layers of porous silicon each having a porosity of about 30% to about 95%.

3. The apparatus of claim 2, wherein the material has a refractive index of about 3 to about 1.

4. The apparatus of claim 1, wherein the porous material is microporous.

5. The apparatus of claim 1, wherein the porous material is mesoporous.

6. The apparatus of claim 1, wherein the porous material has a thickness of about 10 nm to about 500 µm.

7. The apparatus of claim 1, wherein the structure further comprises one or materials selected from the group consisting of metals, crystals, polymers, and optical glass, the material disposed adjacent to the substrate.

8. The apparatus of claim 7, wherein the metal is selected from the group consisting of aluminum, copper, gold, iridium, nickel, palladium, platinum, rhodium, silver, steel, titanium, tungsten, zinc, and alloys thereof.

9. The apparatus of claim 7, wherein the crystal is selected from the group consisting of magnesium fluoride, calcium fluoride, quartz, diamond, sapphire, germanium, and ZnSe.

10. The apparatus of claim 7, wherein the polymer is selected from the group consisting of polydimethylsiloxane and plastics.

11. The apparatus of claim 1, wherein the substrate comprises a plurality of layers of the porous material.

12. A method of performing Raman spectroscopy, the method comprising:
(a) positioning a sample adjacent to a structure comprising a substrate, the substrate comprising porous silicon wherein the porous silicon exhibits a conversion efficiency of less than about 0.0001% per nm in a wavelength range between about 850 nm and about 1020 nm;
(b) directing light from a light source onto the substrate and the sample; and,
(c) measuring an intensity of any Raman scattered light from the sample and the substrate.

13. The method of claim 12 further comprising:
(d) producing an electronic signal proportional to the intensity of the Raman scattered light in a fixed wavelength range or as a function of a wavelength.

14. The method of claim 13 further comprising:
(e) translating the electronic signal into a Raman spectrum.

15. The method of claim 12, wherein the light from the light source has a wavelength in the near-infrared region.

16. The method of claim 15, wherein the light from the light source has a wavelength in a range of about 850 nm to about 1020 nm.

17. The method of claim 12, wherein the porous silicon is a p-type silicon and the substrate comprises a plurality of layers of porous silicon each having a porosity of about 30% to about 95%.

18. The method of claim 17, wherein the material has a refractive index of about 3 to about 1.

19. The method of claim 12, wherein the porous material is microporous.

20. The method of claim 12, wherein the porous material is mesoporous.

21. The method of claim 12, wherein the porous material has a thickness of about 10 nm to about 500 µm.

22. The method of claim 12, wherein the structure further comprises one or materials selected from the group consisting of metals, crystals, polymers, and optical glass, the material disposed adjacent to the substrate.

23. The method of claim 22, wherein the metal is selected from the group consisting of aluminum, copper, gold, iridium, nickel, palladium, platinum, rhodium, silver, steel, titanium, tungsten, zinc, and alloys thereof.

24. The method of claim 22, wherein the crystal is selected from the group consisting of magnesium fluoride, calcium fluoride, quartz, diamond, sapphire, germanium, and ZnSe.

25. The method of claim 22, wherein the polymer is selected from the group consisting of polydimethylsiloxane and plastics.

26. The method of claim 12, wherein the substrate comprises a plurality of layers of the porous material.

27. A Raman scattering structure comprising a substrate, the substrate comprising a plurality of layers of porous silicon, wherein the porous silicon exhibits a conversion efficiency of less than about 0.0001% per nm in a wavelength range between about 850 nm and about 1020 nm.

28. The structure of claim 27, wherein the porous silicon is p-type porous silicon and each of the layers has a porosity of about 30% to about 95%.

29. The structure of claim 27, wherein the porous material has a thickness of about 10 nm to about 500 µm.

30. The structure of claim 27, further comprising a metal selected from the group consisting of aluminum, copper, gold, iridium, nickel, palladium, platinum, rhodium, silver, steel, titanium, tungsten, zinc, and alloys thereof.

31. The structure of claim 27, wherein the porous silicon has a refractive index of about 3 to about 1.

* * * * *